(12) United States Patent
Lund et al.

(10) Patent No.: US 8,945,045 B2
(45) Date of Patent: Feb. 3, 2015

(54) NEEDLELESS INJECTION DEVICE COMPONENTS, SYSTEMS, AND METHODS

(75) Inventors: Jonathan J. Lund, Minnetonka, MN (US); Richard G. Rhode, Minnetonka, MN (US)

(73) Assignee: AMS Research Corporation, Minnetonka, MN (US)

( * ) Notice: Subject to any disclaimer, the term of this patent is extended or adjusted under 35 U.S.C. 154(b) by 638 days.

(21) Appl. No.: 13/262,525

(22) PCT Filed: Jul. 20, 2010

(86) PCT No.: PCT/US2010/042571
§ 371 (c)(1),
(2), (4) Date: Sep. 30, 2011

(87) PCT Pub. No.: WO2011/011392
PCT Pub. Date: Jan. 27, 2011

(65) Prior Publication Data
US 2012/0109049 A1    May 3, 2012

Related U.S. Application Data

(60) Provisional application No. 61/226,833, filed on Jul. 20, 2009, provisional application No. 61/226,803, filed on Jul. 20, 2009.

(51) Int. Cl.
*A61M 5/30* (2006.01)
*A61M 5/142* (2006.01)
(Continued)

(52) U.S. Cl.
CPC ....... *A61M 5/142* (2013.01); *A61M 2025/0024* (2013.01); *A61M 2025/0058* (2013.01);
(Continued)

(58) Field of Classification Search
CPC . A61M 5/30; A61M 5/425; A61M 2005/208; A61M 2210/1078
USPC ...................................................... 604/68–72
See application file for complete search history.

(56) References Cited

U.S. PATENT DOCUMENTS 4,093,108 A    6/1978  Hein et al.
4,130,119 A    12/1978 Sessions et al.
(Continued)

FOREIGN PATENT DOCUMENTS

WO    WO9616606 A1    6/1996
WO    WO9736625 A1    10/1997
(Continued)

*Primary Examiner* — Nicholas Lucchesi
*Assistant Examiner* — Diva K Chander
(74) *Attorney, Agent, or Firm* — Kagan Binder, PLLC (57) ABSTRACT

A needleless fluid injection system include a working shaft (14) with a proximal end and a distal end, an injection shaft with a proximal end and a distal end, and a tissue tensioning mechanism (40) positioned at the distal end of at least one of the working shaft and the injection shaft. Embodiments of the tissue tensioning mechanism can include one or more of multiple radially expanding arcuate members (44), a linearly compressible element (60) with first and second plates at opposite ends of the linearly compressible element, an arcuate member (70) having a first end engaged within the lumen of the injection shaft and a second end moveable relative to the first end, first and second wedges (90a, b) that are slideable relative to each other, an inflatable bladder (110) with a foam material within a body opening of the bladder, at least two electromagnetic coils (146,148), or an electroactive polymer portion (166).

12 Claims, 7 Drawing Sheets

(51) Int. Cl.
  *A61M 25/00* (2006.01)
  *A61M 25/02* (2006.01)
  *A61M 25/10* (2013.01)

(52) U.S. Cl.
  CPC .................. *A61M2025/0293* (2013.01); *A61M 2025/1015* (2013.01); *A61M 2025/1047* (2013.01); *A61M 2210/1078* (2013.01)
  USPC ......................................................... 604/68

(56) References Cited

U.S. PATENT DOCUMENTS

| | | | |
|---|---|---|---|
| 4,742,817 A | 5/1988 | Kawashima et al. | |
| 4,946,442 A | 8/1990 | Sanagi | |
| 5,007,897 A | 4/1991 | Kalb | |
| 5,116,313 A | 5/1992 | McGregor | |
| 5,261,889 A | 11/1993 | Laine et al. | |
| 5,336,178 A | 8/1994 | Kaplan | |
| 5,415,637 A | 5/1995 | Khosravi | |
| 5,693,016 A | 12/1997 | Gumaste et al. | |
| 5,840,062 A | 11/1998 | Gumaste et al. | |
| 5,954,689 A * | 9/1999 | Poulsen ........................ | 604/71 |
| 6,030,406 A | 2/2000 | Davis et al. | |
| 6,203,533 B1 | 3/2001 | Ouchi | |
| 6,210,378 B1 | 4/2001 | Ouchi | |
| 6,238,336 B1 | 5/2001 | Ouchi | |
| 6,280,413 B1 | 8/2001 | Clark et al. | |
| 6,280,414 B1 | 8/2001 | Shah et al. | |
| 6,400,980 B1 | 6/2002 | Lemelson | |
| 6,537,205 B1 | 3/2003 | Smith | |
| 6,547,767 B1 | 4/2003 | Moein | |
| 6,641,553 B1 | 11/2003 | Chee et al. | |
| 6,706,052 B1 | 3/2004 | Chin | |
| 6,783,509 B1 * | 8/2004 | Landau et al. .................. | 604/70 |
| 6,802,826 B1 * | 10/2004 | Smoliarov et al. ............ | 604/192 |
| 6,905,475 B2 | 6/2005 | Hauschild et al. | |
| 7,087,035 B2 * | 8/2006 | Trautman et al. ............... | 604/22 |
| 7,749,156 B2 | 7/2010 | Ouchi | |
| 8,652,095 B2 * | 2/2014 | Stroem Hansen et al. ...... | 604/68 |
| 2003/0163111 A1 | 8/2003 | Daellenbach | |
| 2004/0030320 A1 | 2/2004 | Chee et al. | |
| 2004/0153048 A1 | 8/2004 | Vigil et al. | |
| 2004/0162528 A1 | 8/2004 | Horvath et al. | |
| 2005/0192530 A1 | 9/2005 | Castellano | |
| 2005/0228225 A1 | 10/2005 | Hauschild et al. | |
| 2006/0041225 A1 | 2/2006 | Wallace et al. | |
| 2006/0058815 A1 | 3/2006 | Mickley et al. | |
| 2006/0129125 A1 | 6/2006 | Copa et al. | |
| 2007/0021716 A1 * | 1/2007 | Hansen .......................... | 604/68 |
| 2007/0167921 A1 | 7/2007 | Burren et al. | |
| 2007/0225554 A1 | 9/2007 | Maseda et al. | |
| 2008/0114203 A1 | 5/2008 | Crank | |
| 2008/0119784 A1 | 5/2008 | Roychowdhury | |
| 2008/0119823 A1 | 5/2008 | Crank | |
| 2008/0281261 A1 * | 11/2008 | Steinway et al. ............... | 604/68 |
| 2009/0124974 A1 | 5/2009 | Crank et al. | |
| 2009/0227942 A1 * | 9/2009 | Stroem Hansen et al. ...... | 604/68 |
| 2009/0312696 A1 | 12/2009 | Copa et al. | |
| 2011/0015614 A1 | 1/2011 | Rykhus, Jr. et al. | |
| 2011/0046600 A1 | 2/2011 | Crank | |
| 2011/0295232 A1 * | 12/2011 | Slate et al. .................... | 604/506 |

FOREIGN PATENT DOCUMENTS

| | | |
|---|---|---|
| WO | WO0040279 A1 | 7/2000 |
| WO | WO0066199 A1 | 11/2000 |
| WO | WO0136029 A1 | 5/2001 |
| WO | WO0207812 A2 | 1/2002 |
| WO | WO2004071612 A2 | 8/2004 |
| WO | WO 2005/002660 | 1/2005 |
| WO | WO2005094921 A1 | 10/2005 |
| WO | WO2006057604 A1 | 6/2006 |
| WO | WO2006063180 A2 | 6/2006 |
| WO | WO2006076699 A1 | 7/2006 |
| WO | WO2006084821 A2 | 8/2006 |
| WO | WO2006086719 A2 | 8/2006 |
| WO | WO2007038591 A2 | 4/2007 |
| WO | WO2007079152 A2 | 7/2007 |
| WO | WO2010065126 A2 | 6/2010 |
| WO | WO2010065127 A2 | 6/2010 |
| WO | WO2010065133 A2 | 6/2010 |
| WO | WO2010074705 A2 | 7/2010 |
| WO | WO2010077271 A2 | 7/2010 |
| WO | WO2011011423 A1 | 1/2011 |

* cited by examiner

Fig. 20

NEEDLELESS INJECTION DEVICE COMPONENTS, SYSTEMS, AND METHODS

CROSS-REFERENCE TO RELATED APPLICATION

This application claims benefit from International Application No. PCT/US2010/042571, which was filed on Jul. 20, 2010, which in turn claims priority under 35 U.S.C. §119(e) to U.S. Provisional Application No. 61/226,803, filed Jul. 20, 2009, titled, "Electro-Apposition for an Injection Catheter"; and U.S. Provisional Application No. 61/226,833, filed Jul. 20, 2009, titled, "Injection Catheter Apposition and Tissue-Tensioning System", the entire contents of which are both incorporated herein by reference in their entireties.

TECHNICAL FIELD

The present invention relates generally to the delivery of therapeutic fluids to a treatment site within a patient. More specifically, the invention relates to methods and devices for treating tissue within the human body using a pressurized injection system that accurately delivers therapeutic fluids to a desired location, such as the urinary tract of a patient.

BACKGROUND

A wide variety of medical treatments utilize the delivery and introduction of therapeutic compositions to a treatment location in a patient. In home or outpatient settings, the delivery methods used can include procedures such as oral delivery or inhalants, while in clinical or hospital types of settings, a therapeutic fluid is often injected using a needle-based system. In more complicated methods, a fluid can be delivered surgically through a tubular device, such as a catheter or endoscope, and in some cases, the surgical method can involve minimally invasive procedures.

For minimally invasive procedures, a number of systems have been developed for delivering therapeutic fluids to treatment sites within a patient that include minimally invasive, tubular delivery lumens (e.g., catheters or endoscopes) and pressurized fluid sources. In some cases, these fluid sources include a syringe-like structure that is actuated by a plunger. This plunger can be controlled via a console having control features that help the user to control the amount of pressurized fluid that is delivered to and/or expelled from the system. These systems can include needleless fluid injection systems, for example. Needleless devices and methods for treating tissue of the urinary tract are discussed, for example, in U.S. Patent Application Publication No. 2009/0312696 (Copa et al.), and U.S. Patent Application Publication No. 2006/0129125 (Copa et al.), the entire disclosures of which are incorporated herein by reference. One particular application for needleless fluid delivery systems is for treatment of diseases of the prostate, such as prostatitis, benign prostatic hyperplasia, and prostatic carcinoma.

Needleless fluid delivery systems can include the use of a tube-like device, such as an elongated catheter tube, which is configured to provide a jet-injection of a therapeutic fluid at a desired treatment site. Generally, a needleless injector is used to deliver the therapeutic fluid that is provided from an external reservoir that is located at a proximal end of the tube-like device. The actual fluid administration occurs at a distal end of the tube-like device. Due to the relatively long travel length of the therapeutic fluid through the tube-like device, an injector must generally be capable of pressurizing the therapeutic fluid to a relatively high pressure in order to achieve a certain desired fluid delivery pressure at the distal end of the device.

For any injection or injected tissue, therapeutic agents are desirably delivered with minimal discomfort and procedure time, and with the best possible degree of accuracy of delivery location and delivery volume, and with uniform and accurate distribution of a fluid throughout injected tissue. Further, due to the characteristics associated with the delivery of therapeutic compositions to treatment locations in a patient, there is a need to provide improved procedures, systems, and components for fluid delivery using needleless fluid delivery systems. Such procedures, systems, and components can provide for accurate and controlled dispensing of therapeutic compositions to specific treatment locations within a patient. In particular, there exists a continuing need to provide improved devices for delivering therapeutic fluids to different tissues such as locations of the urinary tract including the bladder, bladder neck, prostate, urethra, kidneys, and ureters.

SUMMARY

The invention generally involves needleless fluid injection devices, systems, and methods. These devices and systems allow for targeted delivery of therapeutic fluids at desired anatomical tissue locations, such as locations in the male or female urinary tract. The therapeutic fluids can include biologically active species and agents such as chemical and biochemical agents, for example. Exemplary devices are designed to deliver fluid at various tissue locations, and can further deliver multiple different therapeutic fluids having varying material properties (e.g., viscosity) using a single system. The devices can be capable of delivering precise amounts of fluid for injection at precise locations and at specific pressures to a location in the patient.

Embodiments of the described invention involve a fluid delivery system with an injector source and an access device. The access device can comprise a minimally invasive, tubular delivery lumen such as a catheter or endoscope. The injector source can include a non-metal, polymeric tube-like device for delivering a therapeutic fluid to a treatment site within a patient. The tube-like device can further include one or more apposition devices that can be activated to force the injection orifice or orifices of the tube-like device against the target tissue. In various embodiments, devices as described can be useful for injecting tissue at different tissue depths and in any desired direction (relative to a surface of the injected tissue), including relatively deep injection of fluid into tissue of any size or depth, or for shallow injection of fluid into tissue at a depth near a tissue surface, such as if the tissue is of a limited depth. Depending on the desired injection depth, orifices can be oriented at different locations along a length of a shaft and at different directions or angles relative to the shaft.

Other embodiments of devices of the invention include a tissue tensioner attached to a distal end of a shaft, which may be a working shaft or an injection shaft. In certain embodiments, a tissue tensioner can be attached (removably or non-removably) to a distal end of an injection shaft, and the injection shaft can be inserted into a working lumen of a working shaft. Optionally, a proximal end of the injection shaft can be inserted into a distal end of the working lumen (alternately a distal end of the injection shaft can be inserted into a proximal end of the working lumen) and the injection shaft can be placed within the length of the working lumen.

In one aspect of the invention, a needleless fluid injection system is provided comprising a working shaft comprising a proximal end and a distal end, an injection shaft comprising a proximal end and a distal end, the injection shaft in operative engagement with the working shaft, and a tissue tensioning mechanism positioned at the distal end of at least one of the working shaft and the injection shaft. In one embodiment; the tissue tensioning mechanism comprises multiple radially expanding arcuate members. In another embodiment, the tissue tensioning mechanism comprises a linearly compressible element, and first and second plates at opposite ends of the linearly compressible element. In another embodiment, the tissue tensioning mechanism comprises an arcuate member having a first end engaged within the lumen of the injection shaft and a second end moveable relative to the first end. In another embodiment, the tissue tensioning mechanism comprises first and second wedges that are slideable relative to each other to change the outer dimensions of the tissue tensioning mechanism. In another embodiment, the tissue tensioning mechanism comprises an inflatable bladder with a foam material within a body opening of the bladder. In another embodiment, the tissue tensioning mechanism comprises at least two electromagnetic coils. In yet another embodiment, the tissue tensioning mechanism comprises an electroactive polymer portion.

BRIEF DESCRIPTION OF THE DRAWINGS

The present invention will be further explained with reference to the appended Figures, wherein like structure is referred to by like numerals throughout the several views, and wherein.

DETAILED DESCRIPTION

The invention relates to devices and methods useful for injecting fluid into tissue for treatment. The fluid can be injected without the use of a needle and can therefore be referred to as a "needleless" fluid injection system. Needleless fluid injection systems of the invention can include one or more orifices that deliver fluid in the form of a jet or fluid stream without a needle passing into the tissue. This fluid is delivered at a pressure, velocity, and stream size that allow the fluid stream to pass through a tissue surface, penetrate into the bulk of the tissue below the tissue surface, and become dispersed as fluid particles within the tissue, such as in the form of a cloud of dispersed fluid particles or droplets. The type of tissue injected for treatment can be any amenable tissue, such as tissue at or near the urinary tract (e.g., tissue of the prostate, kidneys, ureters, urethral tissue, bladder, or other tissues such as heart tissue).

Needleless devices of the type described herein generally include a distal end and a proximal end. As used herein, a "distal end" of a device or system refers to an end area or portion of the device or system that can be introduced within a patient's body during a treatment procedure. For example, elongate shafts or catheters of the needleless injection systems of the invention generally include a distal end that is the first portion of the device that is inserted into the patient for treatment. The distal end may include functional features that operate on fluid or tissue during use, such as one or more orifices, delivery heads (e.g., end effectors, nozzles, etc.) that house one or more orifices, a frictional tissue holding tip, tissue tensioners, lighting or other optical features, steering features, and the like.

As used herein, a "proximal end" of an exemplary needleless device or system is the end that is generally opposite the distal end of that device or system. It is noted that each individual component of a system can include its own proximal and distal ends, while the overall system can also include proximal and distal ends. For one example, a needleless fluid injection system of the invention can include an injector body or console at a proximal end that remains external to the patient during use and an elongate shaft or catheter tube at a distal end. One or more injection orifices at the distal end can be in fluid communication with the console.

An exemplary console used with systems of the invention can include a housing that connects to or is otherwise (directly or indirectly) in fluid communication with an elongate shaft or catheter tube. The console can include fluid that can be pressurized by a pressure source to cause the fluid to flow through the shaft for injection into tissue at the distal end. A device can eject fluid from one or multiple ejection orifices that can be located at the distal end of the shaft or catheter tube.

The fluids that are injected into tissue using systems of the invention may be referred to as an "injectate" or "injection fluid", which may be any type of fluid such as a therapeutic fluid. A fluid stream or jet of injectate can be of a size (e.g., diameter), velocity, pressure, and volume to allow the fluid stream to penetrate directly through a tissue surface, then disperse within the tissue. The stream can be considered to be a relatively high velocity, high pressure, small diameter jet that after entry through a tissue surface, disperses within the tissue, preferably as a multi-directional collection of particles (e.g., a "cloud") or droplets within the bulk of the tissue. Exemplary pressures of a fluid at a pressure chamber can be at least 200 pounds per square inch (psi), and in some embodiments can range from 300 to 5000 pounds per square inch (psi) or more.

In certain embodiments, a tissue tensioner (e.g., as part of a tissue tensioner assembly) can be attached (removably or non-removably) to a distal end of an injection shaft, and the injection shaft can be inserted into a working lumen of a working shaft. Optionally, a proximal end of the injection shaft can be inserted into a distal end of the working lumen (alternately a distal end of the injection shaft can be inserted into a proximal end of the working lumen) and the injection shaft can be placed within the length of the working lumen. The tissue tensioner assembly may include an elongate actuating shaft or mechanism that extends to a proximal end, and a proximal end of this elongate shaft or actuating mechanism can also be inserted into a distal end of the working lumen.

In alternate embodiment, a tissue tensioner (e.g., in the form of a tissue tensioner assembly) can be attached to a distal end of a working shaft, such as by use of a fitting and in a removable or non-removable fashion. An injection shaft can be associated with the working shaft; for example an injection shaft can be secured adjacent to the working shaft, lengthwise along an external surface of the working shaft, optionally by attachment to the same fitting that attaches to the working shaft and to the tissue tensioner. Alternately an injection shaft may be placed permanently, removably, integrally, securely, or movably, within a working shaft, such as but not necessarily within a working lumen. A number of different tissue tensioner embodiments are described herein, and it is understood that while the descriptions may describe attachment of these tissue tensioners to an injectate shaft, the tissue tensioners can alternatively or additionally be attached to a working shaft, which may in turn be associated with an injection shaft.

Figure 1:
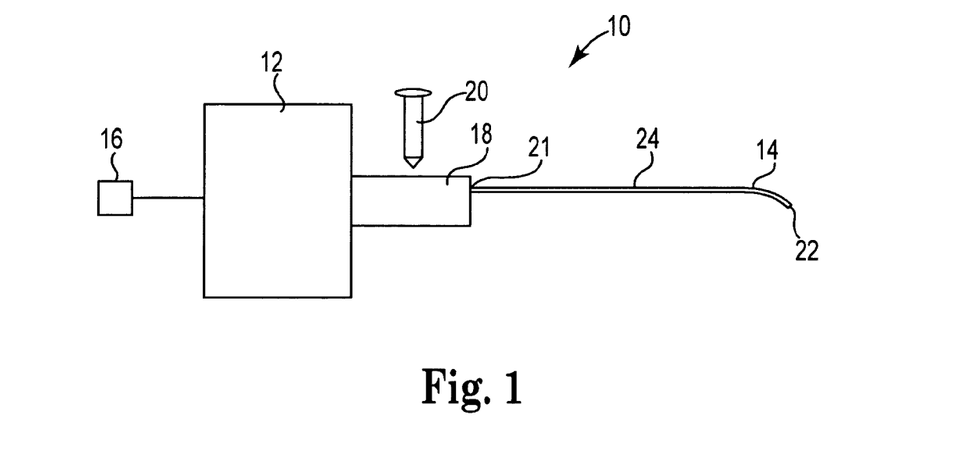
FIG. 1 is a schematic illustration of one embodiment of a needleless fluid delivery system for delivering a therapeutic fluid to a treatment location, in accordance with the invention.

Referring now to the Figures, wherein the components are labeled with like numerals throughout the several Figures, and initially to FIG. 1, one exemplary configuration of a needleless fluid delivery system 10 is schematically illustrated. Delivery system 10 generally includes an injection console 12, an injection chamber 18 in operative communication with the console 12, and a catheter tube or injectate shaft 14 that is also in operative communication with the console 12. The console 12 includes a user interface 16, which can be used for activating and controlling the activities of the various components of the delivery system 10. The user interface 16 can include an input means for selectively delivering a volume of pressurized fluid through the injection chamber 18. The user interface 16 may further include one or more actuatable devices, such as a foot petal, a hand activated controller, switches, buttons, and/or the like. It is also contemplated that the user interface 16 can include a touch-screen that is capable of receiving touch commands and may optionally include a display system for displaying information such as the mode of operation that is being used and/or certain operating parameters of the system.

Although console 12 can include a wide variety of features, any console used in the fluid delivery systems of the invention can generally include a housing, a pressure chamber, and a pressure source. A console can have any configuration, size, or design, ranging from a small, hand-held design to a relatively large floor or table-mounted console. The consoles can also include separate or separable components such as a pressure chamber or injection chamber that can be attached, used for an injection procedure, and detached and then optionally discarded or sterilized and reused. A shaft or catheter tube can also be attached to a console or a pressure chamber in a manner that facilitates separation and optional re-attachment or disposal.

With continued reference to FIG. 1, a proximal or supply end 21 of the catheter tube or injectate shaft 14 extends from a distal end of the injection chamber 18. The shaft 14 may be permanently attached or connected to the injection chamber 18 so that the shaft 14 and chamber 18 are provided to the system as a single component. Alternatively, shaft 14 may be attachable and detachable from injection chamber 18, such as with quick connection fittings, so that the injection chamber 18 and shaft 14 are provided to the system as separate components. Injectate shaft 14 further includes a delivery or distal end 22, which is generally opposite the proximal or supply end 21.

Injectate shaft 14 may include multiple lumens, attachments, or other components that may extend along all or part of the length of the tube. Injectate shaft 14 may further comprise a number of different configurations, such as an endoscope or other catheter configuration, for example. Shaft 14 can further comprise a flexible, elongated attachment tube 24 to allow for easy positioning of the delivery or distal end 22 within the patient.

Delivery or distal end 22 of shaft 14 can comprise a number of different configurations, which can be designed to provide treatment to a specific location in the patient's body (e.g., a rectal treatment location, a gastrointestinal treatment location, a nasal treatment location, a bronchial treatment location, or an esophageal treatment location). The configuration of this distal end 22 is designed and/or selected to provide different types of treatment, such as can be provided by end-fire applicators or side-fire applicators.

Figure 2:
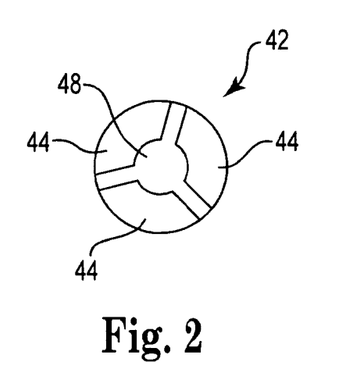
FIG. 2 is a schematic top view of an apposition or tissue-tensioning mechanism for an injection catheter system, the mechanism comprising a plurality of segments in a relatively compressed configuration, in accordance with the invention.
Figure 3:
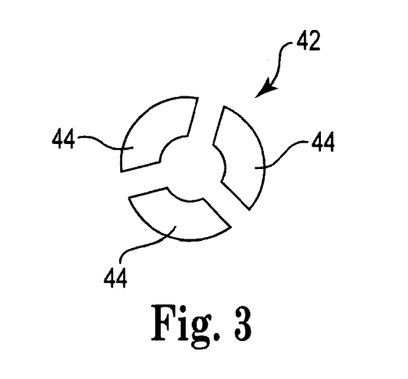
FIG. 3 is a schematic top view of the apposition or tissue-tensioning mechanism of FIG. 2, wherein the plurality of segments are in a relatively expanded configuration.
Figure 4:
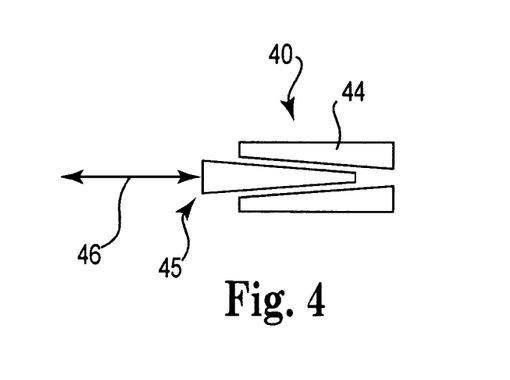
FIG. 4 is a side view of the apposition or tissue-tensioning mechanism of FIGS. 2 and 3.

FIGS. 2-4 illustrate one embodiment of an apposition and/or tissue-tensioning mechanism 40 of the invention. Such a tissue-tensioning mechanism can be provided as part of a tissue tensioner assembly and can be attached (removably or non-removably) to a distal end of an injection shaft. This injection shaft can in turn be inserted into a working lumen of a working shaft. Optionally, a proximal end of the injection shaft can be inserted into a distal end of the working lumen or alternatively, a distal end of the injection shaft can be inserted into a proximal end of the working lumen, and the injection shaft can be placed within the length of a working lumen. In yet another option, the tissue-tensioning mechanism can be attached removably or permanently to a distal end of a working shaft.

The tissue-tensioning mechanism 40 comprises a tissue tensioner assembly 42, which includes multiple radially expandable members 44 that can provide apposition and tissue tensioning within a body lumen for a fluid injection catheter of the invention. In particular, the radially expandable members 44 of this embodiment comprise a series of arcuate members generally arranged in a circular pattern. When these members 44 are in a compressed configuration, the members 44 are positioned to be touching each other, thereby forming a disc-like member. However, when these members 44 are in an at least partially expanded configuration, the members 44 can still be arranged in a circular pattern, but there will be gaps or spaces between the members 44 so that the overall size of the circular arrangement of members 44 is larger (i.e., it will have a larger diameter and circumference).

A number of techniques and devices can be used to move the members 44 between their expanded and unexpanded positions, wherein a wedge device 45 illustrated in FIG. 4 provides one example of such a device. The wedge device 45 can be advanced into and/or retracted from a center opening 48 of a tube member and the assembly 42 in either or both of the directions indicated by arrow 46, thereby causing the members 44 to move outwardly and/or inwardly, respectively. The wedge device 45 therefore can generally act in a reverse manner to that of a lathe collet. The members 44 can be operated manually, by a solenoid, by an electro-active polymer, or by any other suitable activating process. The assembly 42 can alternatively or additionally be provided with various other mechanisms or portions of the delivery system.

Figure 5:
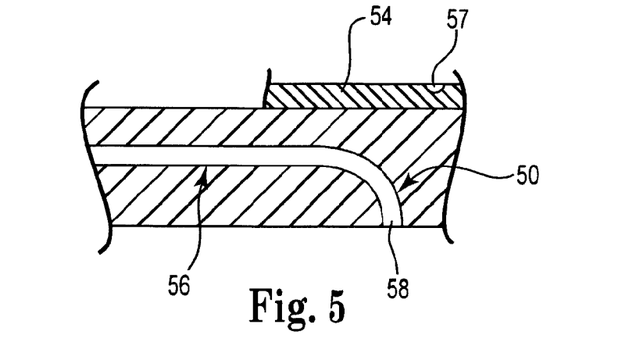
FIG. 5 is a schematic side view of an apposition or tissue-tensioning device that includes a fluid channel feature for an injection cathether system.

FIG. 5 illustrates a fluid channel feature 50 that can be provided at the distal portion of a lumen 54, for example. The feature 50 can be incorporated into an endoscope or the lumen 54, or separately attachable thereto. As can be seen in the figure, the channel feature 50 is provided in fluid communication with a working channel 56 to divert at least a portion of the fluid that is moving to a port 58. The port 58 can be generally positioned opposite an injectate orifice 57 of the lumen 54, such that the fluid exiting the port 58 generates a force that pushes the lumen 54, and its corresponding injectate port, into contact with the tissue or wall of the body lumen in which it is positioned. In this way, the components of the fluid channel feature promote apposition and tissue tension.

Figure 6:
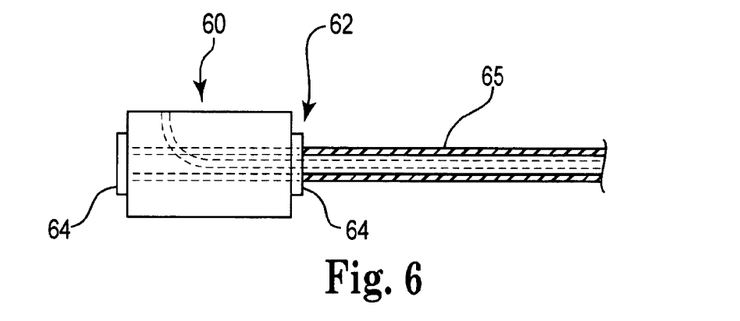
FIG. 6 is a side view of an embodiment of an apposition or tissue-tensioning mechanism including a compressible element.
Figure 7:
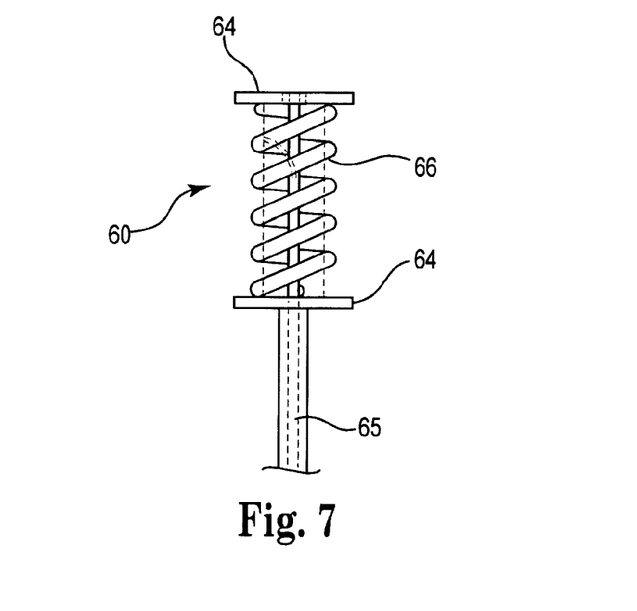
FIG. 7 is a side view of another embodiment of an apposition or tissue-tensioning mechanism including a compressible element.

Another exemplary tissue tensioning or apposition system of the invention is illustrated in FIGS. 6-7. In these figures, a portion of an injection shaft 65 can include a compressible element 60 that is configured to selectively compress and expand to facilitate apposition of the injection shaft with the tissue wall of the body lumen. For one example, the injection shaft 65 can include a mechanism 62 and one or more plates 64, as is illustrated in FIG. 6, for example. The compressible element 60 can be constructed of a relatively soft polymer or rubber material that can be shaped as a cylinder or can instead be arranged as a coil. The element can further be arranged in such a way that movement of the plates 64 toward each other can result in a compression of the element 60, which in turn increases the outer diameter of the element 60 and promotes apposition of the device with the wall of the body lumen in which it is positioned. Other compressible and expandable structures and techniques are contemplated for use with the present invention to promote the disclosed apposition. For example, in another embodiment, which is illustrated in FIG. 7, a compressible coil 66 is provided intermediate the plates 64 in such a way that movement of the plates toward each other will likewise expand the diameter of the coil to promote apposition. In another related embodiment, the outer tube can be twisted to expand the outer diameter of the coil 66.

Figure 8:
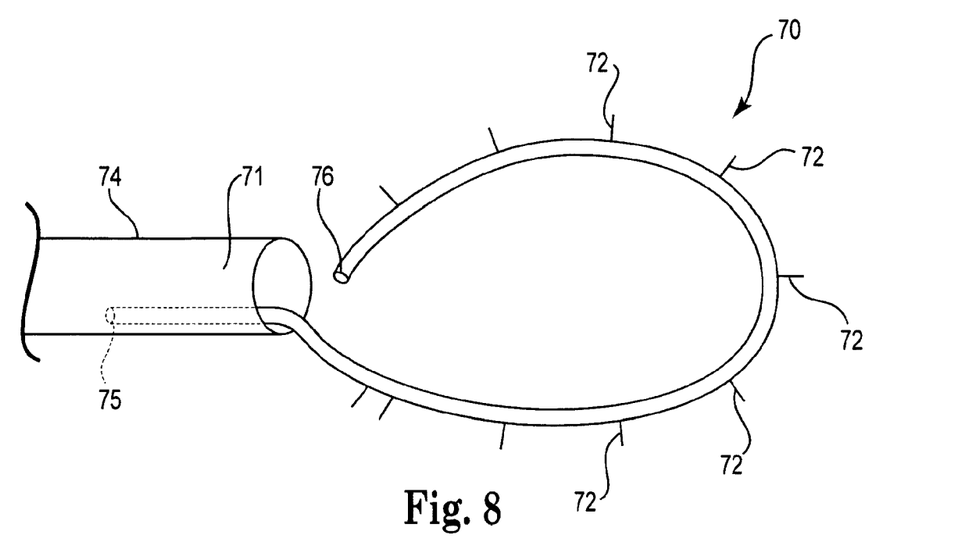
FIG. 8 is a schematic front view of an embodiment of an apposition or tissue-tensioning mechanism for an injection catheter system, the mechanism including an arcuate member.

FIG. 8 illustrates another device for facilitating apposition of an injection shaft 74 (which may include an delivery lumen of the type described above) with an inner wall of a body lumen, and which comprises a deformable and generally arcuate member 70, a portion of which extends from a lumen 71 at a distal end of the shaft 74. Arcuate member 70 comprises a first end 75, a second end 76, and a plurality of injection ports 72 spaced from each other between the first and second ends 75, 76. In this embodiment, first end 75 of member 70 is located within the lumen 71, which may be permanently attached therein or removeably attached, and second end 76 is at least somewhat free to move relative to the shaft 74 and the first end 75 of the member 70, and can be located either inside or outside the shaft 74.

The member 70 is preferably provided with a preformed curve or loop shape, such as may be provided with a shape memory material (e.g., Nitinol). In this way, the member 70 will generally have a curved or loop-like shape in its natural or relaxed configuration, wherein the outer dimensions of the shape of member 70 are equal to or at least slightly larger than the outer diameter of the shaft 74. In addition, the curved or loop-like shape of the member 70 in its relaxed state is generally configured so that its profile width is equal to or at least slightly larger than the inner diameter of the body lumen in which it will be positioned. However, the member 70 is deformable (e.g., by the application of an external force) in order to reduce at least one of its dimensions for its initial insertion into the body lumen of a patient. Once any external forces are removed, the member 70 can move back toward its relaxed state. In this way, the member 70 will be forceably constrained within a body lumen to provide a desired apposition force. Various fluid source connection mechanisms and techniques can be employed to provide pressurized fluid to the lumen 71 and injection ports 72. The shape and dimensions of the member 70 can vary, and can be selectively adapted to fit within and provide constraint against a particular body lumen of the patient. In addition, it is contemplated that greater than one shaped member extends from the distal end of a lumen to provide for additional apposition capabilities.

The injection ports 72 of member 70 can be evenly or otherwise spaced from each other around the periphery of the member 70, and more or less ports 72 can be provided than are illustrated in the Figure. These injection ports 72 are preferably in fluid communication with a fluid source, such as a reservoir, that provides pressurized fluid to the member 70.

Figure 9:
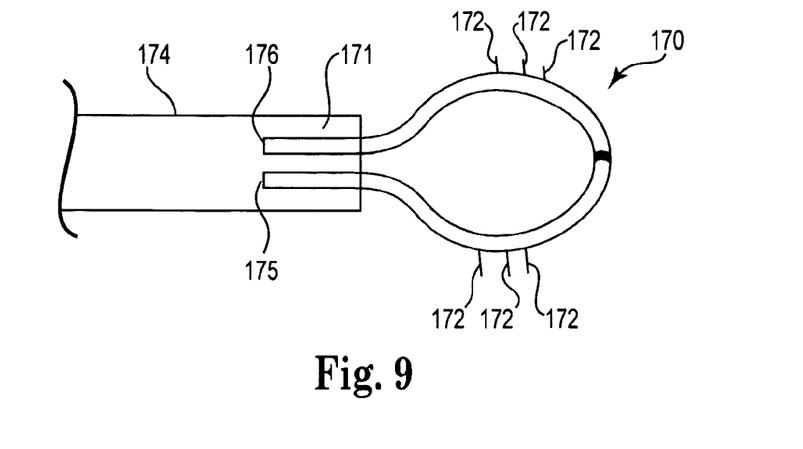
FIG. 9 is another schematic front view of another embodiment of an apposition or tissue-tensioning mechanism for an injection catheter system, the mechanism including an arcuate member.

FIG. 9 illustrates another manner of facilitating apposition of an injection shaft 174 that is similar to that of FIG. 8. In this embodiment, the apposition or tissue-tensioning configuration includes a generally arcuate member 170, a portion of which extends from a lumen 171 at a distal end of the shaft 174. Arcuate member 170 comprises a first end 175, a second end 176, and two sets of injection ports 172 that are spaced on opposite sides of the shaped loop of the arcuate member 170. In this embodiment, first end 175 and second end 176 are positioned within the lumen 171, while a portion of the member 170 extends from an end of the shaft 174 in a loop-like configuration. The member 170 may be provided with a preformed loop or shape, or the shape may be maintained simply by positioning the two ends 175, 176 in their respective locations within the lumen 171, thereby forcing the remaining portion between the ends into an arcuate shape. As with the member 70 described above, the outer dimensions of the shape of member 170 are preferably equal to or at least slightly larger than the outer diameter of the shaft 174 to aid in apposition of the device. In addition, the curved or looplike shape of the member 170 is generally configured so that its profile width is equal to or at least slightly larger than the inner diameter of the body lumen in which it will be positioned. In this way, the member 170 will be forceably constrained within the body lumen to provide a desired apposition force. Both members 70 and 170 can provide a desired number of injection ports and apposition promotion in a structural embodiment that requires relatively few parts, and does not require any additional inflation devices, such as balloons.

Figure 10:
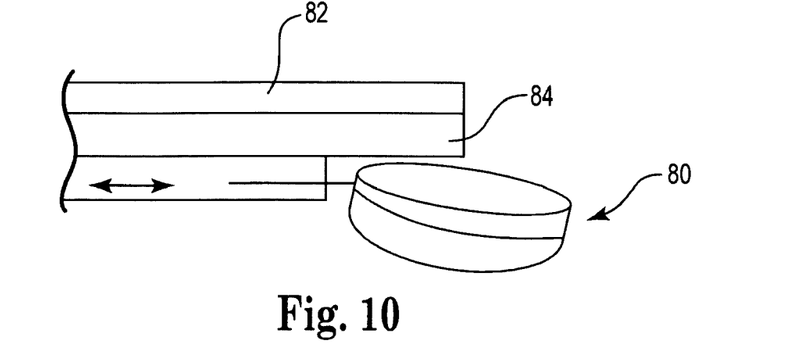
FIG. 10 is a schematic front view of an embodiment of an apposition or tissue-tensioning mechanism having an expandable feature.

FIG. 10 illustrates an embodiment of a portion of a fluid delivery system that includes a compressible and expandable basket or element 80 adjacent its distal end, which is operatively disposed to at least a portion of the system, such as an endoscope 84, an injector lumen 82, and the like. The basket or element 80 can be made of a shape memory material, such as Nitinol, that can be deformed by application of an external force, but that will return to its original shape and/or size after removal of that external force. In operation, the basket or element 80 can be advanced into a body lumen in a sheath or covering, then it can be unsheathed and compressed (e.g., longitudinally) so that the cross-sectional dimension of the basket or element 80 can expand to create apposition of the injector lumen, or other device to which it is attached, within a body lumen. In order to retract or otherwise disengage the injector lumen 82, the basket or element 80 can be selectively expanded to reduce its outer dimensions within the body lumen to a size wherein it can be removed from the body lumen. While Nitinol is described above as one exemplary material from which the basket or element 80 can be made, other shape-memory materials and configurations for the basket or element 80 are contemplated to promote selective apposition and retraction.

Figure 11A:
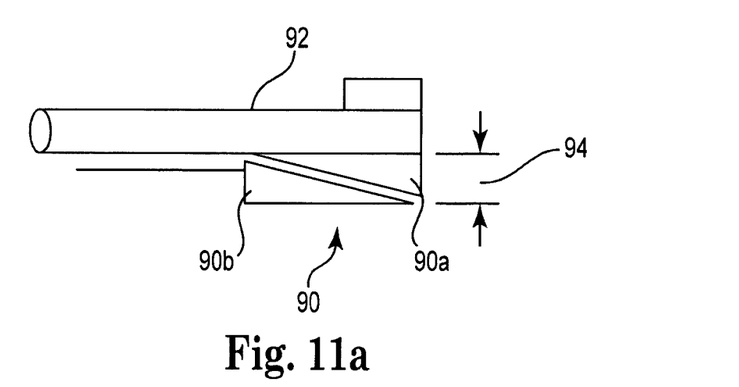
FIG. 11a is a schematic front view of another embodiment of an apposition or tissue-tensioning mechanism including a wedge feature comprising wedges in a first position.
Figure 11B:
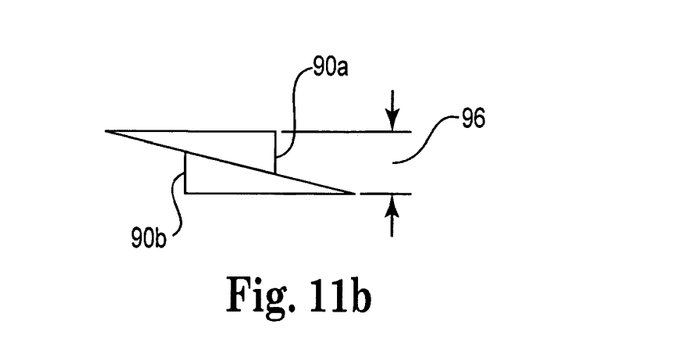
FIG. 11b is a schematic front view of the wedges of FIG. 11a in a second position.

Another embodiment of an apposition feature that can be used with a fluid delivery system of the invention is illustrated in FIGS. 11a-11b. In this embodiment, the delivery system includes a wedge system 90, which includes first and second wedges 90a, 90b. The wedges 90a, 90b are slideably engageable relative to each other to create a selective and variable tissue apposition technique. In particular, the wedges 90a, 90b can be operatively disposed along a portion of an endoscope or injection lumen, and are provided in operative communication with a lever or other actuator device (not shown). The first and second wedges 90a, 90b are aligned or "ramped" together such that the combined height of these components in a first position is illustrated by reference number 94 in FIG. 11a. The wedges 90a, 90b can then be slideably separated or "unramped" to a second position, as is illustrated in FIG. 11b. In this position, the combined height (shown as reference number 96 in FIG. 11b) of the two components is different than their combined height 94 in their first position. This adjustment of the wedges 90a, 90b relative to each other enables the user to control the outer dimensions of the device to provide the desired apposition within a body lumen, along with retraction relative to the body lumen. Although two exemplary positions of the wedges 90a, 90b are illustrated in the figures, it is understood the wedges can be moved in the opposite direction relative to each other than is shown, and that any number of positions of these components relative to each other (e.g., intermediate the illustrated first and second positions) is possible to achieve a desired height and corresponding apposition of the device to which they are operatively attached.

Figure 12:
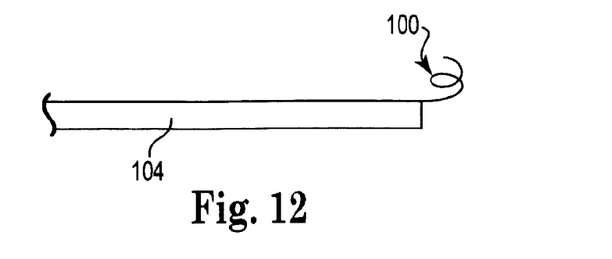
FIG. 12 is a schematic front view of another apposition or tissue-tensioning mechanism including an anchoring member at one end.
Figure 13:
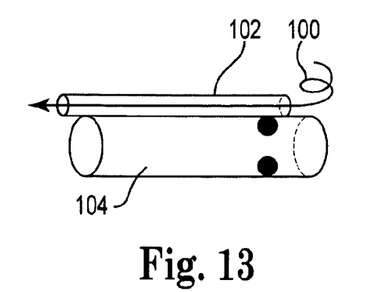
FIG. 13 is a perspective view of an apposition or tissue-tensioning mechanism including an anchoring member at one end.
Figure 14:
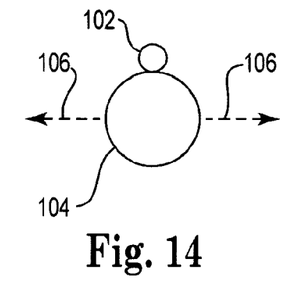
FIG. 14 is an end view of the apposition or tissue-tensioning mechanism of FIG. 13.

FIGS. 12-14 illustrate another embodiment of an apposition configuration of the invention. In particular, a delivery or injection shaft 104 is provided, which includes an attached shaped member 100. In this embodiment, the shaped member 100 is shaped in a helix or pigtail configuration, which can advantageously provide smooth, curved surfaces for contact with the tissue of a body lumen for apposition. However, it is understood that the shaped member 100 may instead have a different shape and/or configuration. The shaped member 100 can be made of a shape-memory material, such as Nitinol, so that it can be deformed and released for insertion, placement, and retraction of the device from the body lumen. The member 100 can be permanently anchored, or can be configured for selective retraction from a body lumen. The system may also include an auxiliary tube or shaft 102 adjacent to the shaft 104, wherein the member 100 can optionally be deformed and held within the tube or shaft 102 until it is desired to deploy the member to provide apposition forces to the delivery or injection shaft 104.

Figure 15:
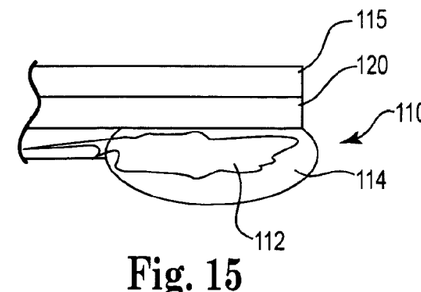
FIG. 15 is a schematic front view of an embodiment of an apposition or tissue-tensioning mechanism including at least one expandable element.
Figure 16:
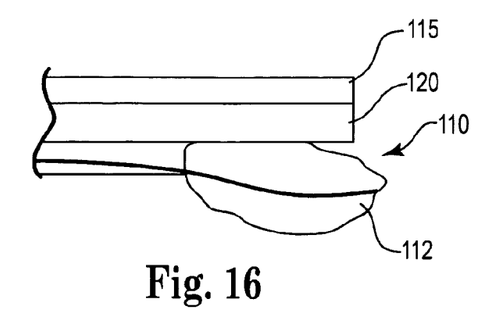
FIG. 16 is a schematic front view of another embodiment of an apposition or tissue-tensioning mechanism including at least one expandable element.

Yet another embodiment of an apposition mechanism in accordance with the invention is illustrated in FIGS. 15 and 16. In this embodiment a delivery system includes a delivery or injection shaft 115, an optional endoscope 120, and an expandable element 110 extending from these components for use as an apposition device. The expandable element 110 can be an inflatable bladder 114 into which a foam material 112 (e.g., polymer foam) is provided. In embodiments where a foam material is provided, the foam may be constructed of a relatively low durometer polyurethane or like material. Expansion of the expandable element 110 via the addition of a certain volume of foam or a filler material into the open space can provide a desired amount of apposition for the device. A vacuum, catheter, or the like can control deployment and positioning of the expandable element 110. Other filler materials and expandable materials can be used, as desired, in accordance with the invention.

Figure 17:
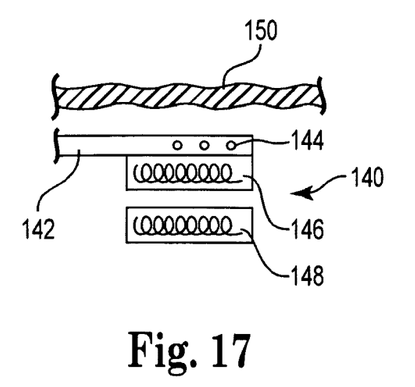
FIG. 17 is a schematic front view of an embodiment of an apposition device comprising electromagnetic properties in a first position relative to tissue.
Figure 18:
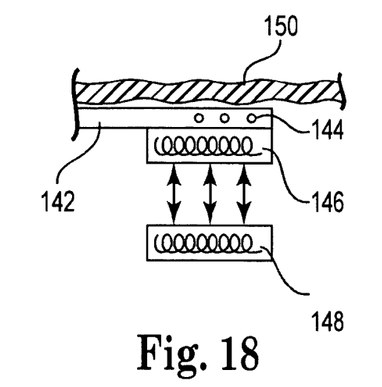
FIG. 18 is a schematic front view of the apposition device of FIG. 17, with the apposition device in a second position in which it is closer to the tissue.

FIGS. 17 and 18 illustrate the use of an "electro-apposition" system 140 configured to use electromagnetic properties or force to promote apposition of a delivery lumen and its associated injectate orifices to the tissue wall of a body lumen. System 140 is schematically illustrated as being adjacent to a fluid delivery catheter 142, which comprises one or more orifices 144 adjacent to its distal end. In one particular embodiment, the system 140 includes multiple (e.g., two) electromagnetic coils 146, 148, with one of the coils 146 being directly attached to or integrated with the catheter 142. The electromagnetic coils 146, 148 can be designed to either repel or attract each other, wherein FIG. 17 illustrates the condition wherein the coils 146, 148 are attracted to each other, and FIG. 18 illustrates the condition wherein the coils 146, 148 repel each other, thereby moving the catheter 142 closer to the tissue it will be treating. In particular, reverse polarity can be introduced to one of the coils 146, 148 to move or otherwise displace the coil 146 and the catheter 142 for apposition with tissue 150 of the body lumen of the patient, as is illustrated in FIG. 18. In this way, the orifices 144 of the catheter 142 will be positioned for injectate fluid delivery to the tissue 150.

Figure 19:
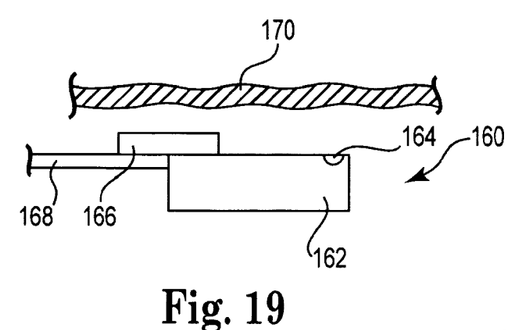
FIG. 19 is a schematic front view of an embodiment of an apposition device comprising an electroactive polymer in a first position relative to tissue.
Figure 20:
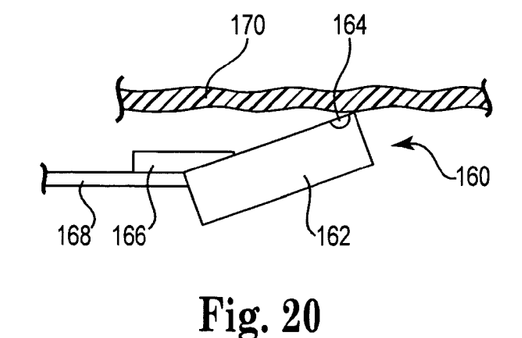
FIG. 20 is a schematic front view of the apposition device of FIG. 19, with the apposition device in a second position in which it is closer to the tissue.

Another embodiment of an apposition system 160 is illustrated in FIGS. 19 and 20, which generally includes a fluid delivery catheter 162 with at least one orifice 164 adjacent to its distal end. An electroactive polymer portion 166 is attached to or integrated with the catheter 162, such as at a distal and of the catheter 162. The electroactive portion 166 can be designed to either maintain the delivery catheter 162 in an aligned configuration relative to the length of the device or to shorten or otherwise deform in such a way that it causes the delivery catheter 162 to be at an angle relative to the length of the device. In particular, FIG. 19 illustrates the configuration wherein the electroactive portion 166 is generally aligned with the catheter 162 and spaced from the adjacent tissue 170, while FIG. 20 illustrates the configuration wherein the electroactive portion 166 is activated such that it is shortened or otherwise deformed so that the catheter 162 is angled and positioned to be closer to or in contact with the tissue 170.

Various hinges, linkages, collet-like structures, wedges, push-pull devices, and like mechanisms and techniques can be employed for the electroactive portion 166, which can be implemented to move or otherwise dispose the catheter 162 and its injection ports 164 within the patient's body lumen. The electroactive portion 166 can be used as an actuator for these devices to selectively initiate the movement and apposition of the catheter 162. For example, FIG. 19 illustrates an embodiment of the catheter 162 with the electroactive portion 166 provided between the tissue 170 and the catheter 162, while FIG. 20 illustrates apposition of the catheter 162 upon actuation of the electroactive portion 166 to pivot the catheter 162 toward the tissue 170.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

The invention claimed is:

1. A needleless fluid injection system comprising;
a working shaft comprising a proximal end and a distal end;
an injection shaft comprising a proximal end and a distal end, the injection shaft in operative engagement with the working shaft, and
a tissue tensioning mechanism positioned at the distal end of at least one of the working shaft and the injection shaft, the tissue tensioning mechanism comprising a longitudinal axis and a linearly compressible element, and first and second plates at opposite ends of the linearly compressible element that are moveable relative to each other along the longitudinal axis.

2. The injection system of claim 1, wherein the first and second plates are slideable relative to each other such that decreasing the distance between the plates along the longitudinal axis increases an external dimension of the compressible element in a radial direction.

3. The injection system according to claim 1, wherein the linearly compressible element comprises one of a compressible rubber or soft polymer material.

4. The injection system according to claim 1, wherein the linearly compressible element comprises one of a spring or a coil.

5. The injection system according to claim 1, wherein the injection shaft comprises an injection lumen extending from the proximal end to the distal end of the injection shaft, and further comprising at least at least one injection orifice extending through a wall of the injection lumen proximate the distal end of the injection shaft.

6. The injection system according to claim 1, wherein the proximal end of the injection shaft is in fluid communication with a fluid supply source.

7. A needleless fluid injection system comprising;
a working shaft comprising a proximal end and a distal end;
an injection shaft comprising a proximal end, a distal end, and a lumen extending from its proximal end to its distal end, the injection shaft in operative engagement with the working shaft, and
a tissue tensioning mechanism positioned at the distal end of at least one of the working shaft and the injection shaft, the tissue tensioning mechanism comprising an arcuate member having a first end engaged within the lumen of the injection shaft and a second end moveable relative to the first end.

8. The injection system of claim 7, wherein the arcuate member comprises a shape memory material.

9. The injection system according to claim 7, wherein the arcuate member comprises at least one injection port.

10. The injection system, of claim 9, further comprising a fluid source in fluid communication with the arcuate member.

11. A needleless fluid injection system comprising;
a working shaft comprising a proximal end and a distal end;
an injection shaft comprising a proximal end and a distal end, the injection shaft in operative engagement with the working shaft, and
a tissue tensioning mechanism positioned at the distal end of at least one of the working shaft and the injection shaft, the tissue tensioning mechanism comprising at least two electromagnetic coils.

12. The injection system of claim 11, wherein a first electromagnetic coil is operatively engaged with at least one of the working shaft and the injection shaft, and wherein a second electromagnetic coil is moveable relative to the first magnetic coil.

* * * * *